Dec. 17, 1974
B. J. MACHIN
Plant Pat. 3,660
CHRYSANTHEMUM PLANT
Filed April 12, 1973
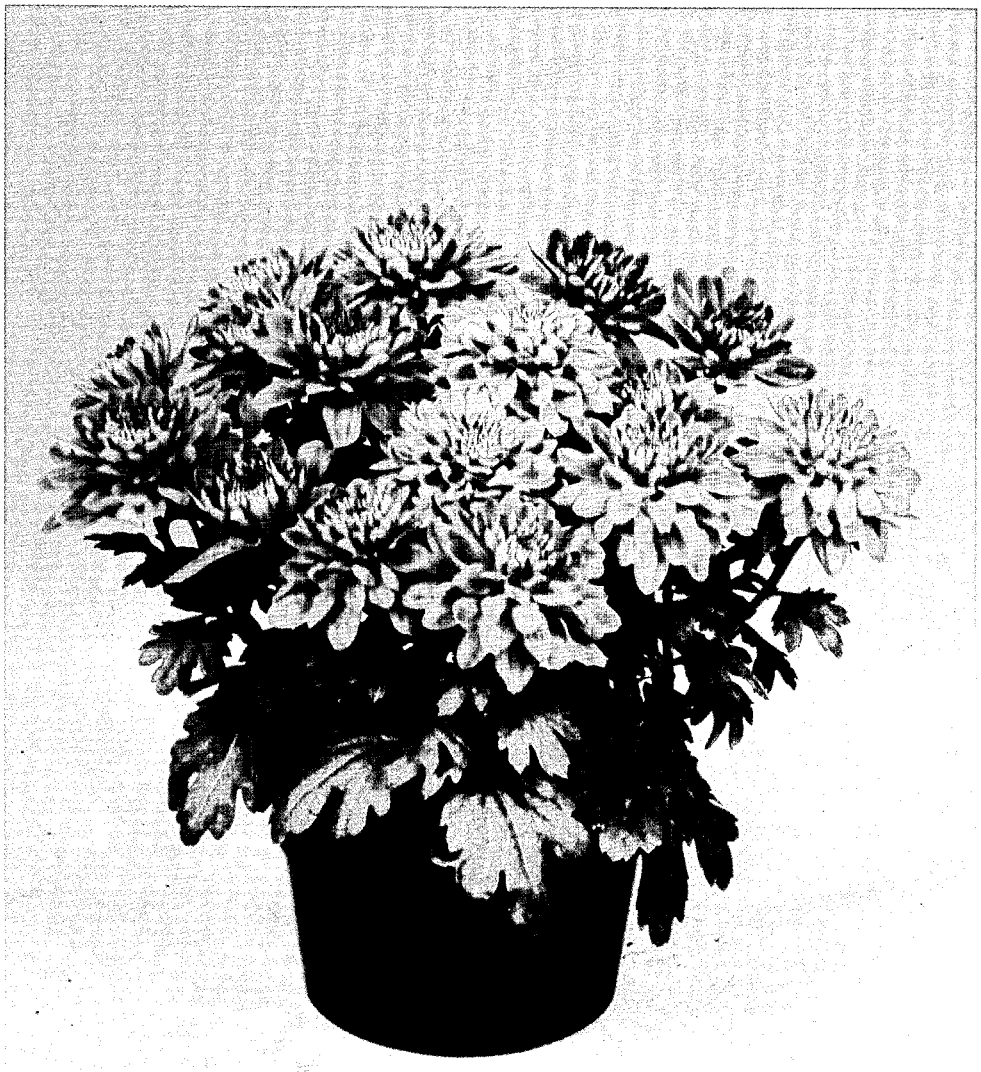

United States Patent Office

Plant Pat. 3,660
Patented Dec. 17, 1974

3,660
CHRYSANTHEMUM PLANT

Barrie John Machin, Chichester, England, assignor to Frampton's Nurseries Limited, Chichester, England Filed Apr. 12, 1973, Ser. No. 350,627
Int. Cl. A01h 5/00
U.S. Cl. Plt.—81 1 Claim This invention relates to a new and distinct variety of *Chrysanthemum morifolium* Bailey (Pot type) known as Artemis.

Artemis is a seedling originated by me from a cross made in 1967 between the variety Redcap and the variety Frolic, the former being the seed parent and the latter being the pollen parent.

The variety Artemis resulted from an extensive breeding program with the object of producing improved varieties for year round pot production with more uniformity and dependability especially during seasons of low light conditions.

Artemis has the following improved characteristics over its seed parent Redcap.

1. It has a stronger habit of growth and produces more shoots on each plant after pinching, especially during the winter months.
2. It has a more uniform response during the winter months.
3. It has a deeper more incurving flower form.

Artemis has the following improved characteristics over its pollen parent Frolic.

1. It bears flowers of deeper color.
2. It bears flowers which are larger in diameter.
3. The quality of petals is higher in winter light conditions.

The accompanying drawing shows a typical flower of my new variety depicted in color as nearly true as it is reasonably possible to make the same in a color illustration of this character.

Asexual reproduction of this new variety Artemis by rooting vegetative shoots in Sussex, England, shows that the above characteristics are fixed and come true to type through succeeding generations.

The following is a detailed description of the new variety Artemis with current terminology in accordance with the Royal Horticultural Society color chart (RHS).

Genus—Chrysanthemum
Species—*Morifolium* Bailey

Type—Pot
Class—Incurving decorative

Breeding: The original seedling was derived from a cross between the variety Redcap and the variety Frolic, the former being the seed parent the latter being the pollen parent. The cross was made in 1967 at Framptons Nurseries Ltd., Forbridge Nursery, Chichester, Sussex, England.

Propagation: Holds its distinguishing characteristics through succeeding propagation by rooting vegetative shoots.

Flower: When grown in Sussex, England, in 3½ in. pots and pinched, up to six flowers per plant are produced. When five plants are planted per 5½ in. pot, 4 to 5 flowers are borne on each plant.

Bloom:

*Size.*—Average diameter is 9 cm. when fully open.

*Petalage.*—Incurving decorative containing 200 to 225 ray petals and up to 20 disc petals.

*Form.*—Incurving decorative.

*Petals.*—Medium length, broad, overlapping and thick.

Color of open bloom:

| | |
|---|---|
| Inner face of fully expanded petal | RHS 70B |
| Outer face of fully expanded petal | RHS 75C |
| Inner face of young petal | RHS 70A |
| Outer face of young petal | RHS 75B |

Response Group: 10 weeks.
Temperature Tolerance: 58°–60° F. for night minimum.
Plant: Stocky, well branched habit of growth.
Foliage: Medium quality and texture. Average internode length 1½–2 cm. Medium size. Color RHS 137A.
Stem: Thick and strong. Color RHS 139D at flowering.

I claim:

1. A new and distinct variety of *Chrysanthemum morifolium* Bailey, substantially as shown and described, characterized particularly as to its novelty by the unique combination of a deep red purple color, a deep incurving flower form, strong and uniform response under winter light conditions, and blooms having an average diameter of about 9 cm. when fully open.

No references cited.

ROBERT E. BAGWILL, Primary Examiner